United States Patent [19]

Desai et al.

[11] Patent Number: 4,867,986

[45] Date of Patent: Sep. 19, 1989

[54] DRY STABILIZED MICROEMULSIFIED OMEGA-THREE ACID-CONTAINING OILS

[75] Inventors: Mahesh Desai, Hawthorne; Frank Molinaro, West Orange, both of N.J.

[73] Assignee: Pharmachem Laboratories, Inc., South Hackensack, N.J.

[21] Appl. No.: 74,935

[22] Filed: Jul. 17, 1987

[51] Int. Cl.$^4$ ................................................. A61K 9/20
[52] U.S. Cl. ................................... 424/464; 424/455; 424/465; 424/470; 424/489; 424/499; 424/502; 426/330.6; 426/417; 426/608; 426/654
[58] Field of Search ............... 424/502, 499, 489, 465, 424/464, 470

[56] References Cited

U.S. PATENT DOCUMENTS

| | | | |
|---|---|---|---|
| 3,959,518 | 5/1976 | Vincent | 426/643 |
| 4,344,976 | 8/1982 | Bladh | 426/472 |
| 4,395,422 | 7/1983 | Schmidt | 424/284 |
| 4,678,808 | 7/1987 | Ward et al. | 514/77 X |

FOREIGN PATENT DOCUMENTS 60-49097  3/1985  Japan .

OTHER PUBLICATIONS

Phillipson et al., N. Engl. J. Med., 312, 1210–16 (1985)
Nestel, Am. J. Clin. Nutr., 43, 752–57 (1986).
"Marine Lipid . . . ", Int. Med. News, 19, 7 (May 15, 1986).
Harris, Contemp. Nutr., 10, 8, 145–46 (Aug. 1985).

*Primary Examiner*—Thurman K. Page
*Attorney, Agent, or Firm*—Davis Hoxie Faithfull & Hapgood

[57] ABSTRACT

Storage-stable, bio-available, free-flowing, microemulsified, Omega-three acid-containing oil compositions in the form of microspheres and macrospheres, said compositions consisting essentially of (1) up to about 70% by weight of Omega-three acid-containing oil, and (2) gelatin, in which the oil is microemulsified by the gelatin; processes for their preparation; and product applications (including tablet-type solid forms, dry powders, and spoonable, drinkable emulsions).

18 Claims, No Drawings

DRY STABILIZED MICROEMULSIFIED OMEGA-THREE ACID-CONTAINING OILS

FIELD OF THE INVENTION

This invention relates to dry, stabilized, free-flowing, microemulsified Omega-three acid-containing oils. In preferred embodiments, this invention relates to dry, stabilized, microemulsified Omega-three acid-containing oils that are rich in eicosapentaenoic acid (EPA) and docosahexaenoic acid (DHA).

BACKGROUND OF THE INVENTION

In recent years, attention has been drawn to marine animal oils as useful foodstuffs for both human and animal consumption. These oils often contain Omega-three fatty acids, particularly EPA and DHA. Omega-three fatty acids are those in which doublebond unsaturation occurs at, and no closer than, the third carbon atom from the end of the acid molecule. Other Omega-three fatty acids include linolenic acid and docosapentaenoic acid (DPA). Linolenic acid is a component of soybeans, linseed and some green, leafy vegetables. In the detailed description below, this invention will be discussed in connection with preferred embodiments where Omega-three acid-containing marine animal oils are used. However, other sources of Omega-three fatty acids, e.g., plants, can also be employed.

The scientific literature has recognized that marine animal oils likely have substantial therapeutic value. Such literature includes, e.g., the following articles: (I) Phillipson, B. E., et al., "Reduction of Plasma Lipoproteins and Aproteins By Dietary Fish Oils In Patients With Hypertriglyceridemia", N. Engl. J. Med. 312: 1210–1216 (1985); (II) Nestel, P. J., "Fish Oil Attenuates The Cholesterol Induced Rise In Lipoprotein Cholesterol," Am. J. Clin. Nutr. 43:752-757 (1986); (III) "Marine Lipid Concentrate Improves Plasma Lipid Levels In CHD", Int. Med. News 19:7 (May 15, 1986); and (IV) Harris, W. S., "Health Effects of Omega-Three Fatty Acids", Contemporary Nutrition 10:8, pp. 145-6 (August, 1985). There is evidence that this therapeutic activity is due in large part to the Omega-three fatty acids.

Among the probable therapeutic benefits of consuming Omega-three acid-containing marine animal oils which find support in the scientific literature are: reduced plasma triglycerides, reduced ischemia, and reduced tissue destruction by auto-immune diseases. Aside from these probable therapeutic benefits, marine animal oils are recognized as edible nutrients, and can be beneficially incorporated into foods for both human and animal consumption.

It is known that Omega-three fatty acids such as EPA and DHA are readily oxidized in the presence of light, oxygen, heat, trace minerals and moisture. When oxidized, these fatty acids become discolored, odoriferous, and less therapeutically active.

Conventionally, marine animal oils have been encapsulated in soft elastic capsules which effectively protect the oil under normal storage conditions. Such a product was recently introduced to the commercial market by Squibb under the trade name PROTOCHOL. A similar product, marketed by Warner-Lambert, is sold under the trade name PROMEGA. A third such product, "MAX EPA", is marketed by RP Scherer N.A. These soft elastic gelatin capsule products consist essentially of a consolidated one-gram dose of marine animal oil encased in gelatin.

In contrast, according to a first embodiment where spray-drying is employed, the products of this invention are microspheres, each microsphere containing, on average, several hundred gelatin-encased marine animal oil microdroplets. According to two additional embodiments where a double dispersion beadlet process or a catch-medium process is used, the products of this invention are macrospheres, each macrosphere being similar in structure to a microsphere except for its greater volume and density. Each macrosphere contains, on average, several thousand gelatin-encased marine animal oil microdroplets.

Japanese patent application disclosure (KOKAI) No. SHO 60-49097, issued Mar. 18, 1985, discloses a marine animal oil product which is microencapsulated, the microcoating consisting essentially of casein and saccharides. The products of the Japanese '097 disclosure are said to be stable for one month when stored at about 5° C. away from light, or for one year at about 5° C. if packaged in a container having oxygen- and ultra violet light-barrier properties.

Despite these advances in the art of packaging Omega-three acid-containing marine animal oils to make them storage-stable and suitable for preparation of tableted dosages, as well as for convenient addition into food products for human and animal consumption, further advances are desirable. In particular, further improvements are needed in long term storage-stability, adaptability to compression for tableting, bio-availability (rapidity with which the microdroplets of oil are released from a microemulsified coating versus from a conventional gelatin capsule), and free-flowing dry structure for ease of handling.

It is an object of this invention to provide an improved dry microemulsified Omega-three acid-containing oil product which is stabilized against deterioration, characterized by improved bio-availability, and which may readily be tableted or otherwise incorporated into food products for human and animal consumption.

It is an additional object of this invention to provide a process for producing dry stabilized microemulsified Omega-three acid-containing oil products.

Further objects will be apparent from the discussion below.

SUMMARY OF THE INVENTION

In accordance with this invention, a storage-stable, bio-available, free-flowing, microemulsified, Omega-three acid-containing oil composition is provided in a form selected from the group consisting of microspheres and macrospheres, said composition consisting essentially of (1) up to about 70% by weight of Omega-three acid-containing oil, and (2) gelatin, in which the oil is microemulsified by the gelatin. The gelatin microemulsifier serves as a barrier to oxygen, shielding the Omega-three acid-containing oil from the atmosphere and retarding its degradation. According to one embodiment, a microsphere composition is produced by spray-drying according to the following steps:

(A) Combining with homogenization, (1) up to about 70% by weight of Omega-three acid-containing oil, and (2) gelatin having a Bloom value between about 25 and about 75, to yield an oil-in-water emulsion thereof;

(B) Homogenizing the emulsion until the maximum observed dispersed particle diameter is about 5 microns or less;

(C) Adding sufficient water to the emulsion so that the combined weight of Omega-three acid-containing oil and gelatin is about 40% to about 50% of the total weight of the emulsion; and (D) Spray-drying the emulsion to yield a dry, microemulsified Omega-three acid-containing oil composition, in which the oil is microemulsified by the gelatin in microspheres having a diameter ranging from about 50 microns to about 400 microns.

According to another embodiment, a storage-stable macrosphere composition is provided consisting essentially of (1) up to about 70% by weight of Omega-three acid-containing oil, and (2) gelatin having a Bloom value between about 25 and about 75, in which the oil is microemulsified by the gelatin. This macrosphere composition is made using a catch-medium process, as discussed below.

According to a further embodiment, a storage-stable macrosphere composition is provided consisting essentially of (1) up to about 70% by weight of Omega-three acid-containing oil, and (2) gelatin having a Bloom value between about 250 and about 300, in which the oil is microemulsified by the gelatin. In this embodiment, the macrospheres are produced by a double dispersion beadlet process.

DETAILED DESCRIPTION

The marine animal oil to be microemulsified may be derived from any desired marine animal source. Among the marine animal oils particularly contemplated for use are sardine, tuna, menhaden, herring, anchovy, mackerel, cod and salmon. The marine animal oils may be used either singly or in combinations.

Preferably, the marine animal oil selected for use is one which is rich in EPA and DHA. Most preferably, the marine animal oil contains at least about 30% of either EPA, DHA, or a mixture thereof. Marine animal oils comprising any greater proportions of Omega-three fatty acids up to 100%, if available, can be employed.

Derivatives of Omega-three fatty acids, e.g. esters and triglycerides, can be prepared from marine animal oils by conventional processes, and they can also be used.

Marine animal oils, although of relatively recent development, are now well known, and their production is readily accomplished by conventional methods. See, for example, Vincent, U.S. Pat. No. 3,959,518, and Bladh, U.S. Pat. No. 4,344,976.

The microemulsifier of this invention is gelatin. Gelatin is a water-soluble protein resulting from the partial hydrolysis of collagen. As hydrolysis is continued, collagen is degraded to gelatin of progressively decreasing gel strength.

Gel strength is conventionally measured by the Bloom gel strength test. The Bloom test is well known, and those skilled in the art will readily employ standard procedures to obtain Bloom gel strength measurements. The lowest Bloom value that can be accurately measured is about 20, which corresponds to an average gelatin molecular weight of about 10,000 grams per mole (g/m). Bloom value varies directly with molecular weight. Hence, the gel strength of gelatin below about 10,000 g/m is expressed in gram molecular weight.

Preferably, the gelatin starting material is granular, e.g. in about the 20-30 mesh range. Powdered gelatin can be used but excessive air entrainment may occur during its addition to water. Coarse grades of gelatin may dissolve in water too slowly for practical use.

Where a spray-drying process is to be used, the gelatin to be employed for microemulsification should have a Bloom gel strength between about 25 and about 75. Gelatin having a gel strength above about 100 exhibits an undesirable stringiness which makes it unsuitable for microemulsification via spray-drying. The product in that case will exit from the spray-atomizer as a cotton candy-like material or as flakes, rather than as microspheres. Gelatin having extremely low Bloom strength can be produced e.g., by strenuous enzymatic degradation (as will be explained below). Such gelatin, e.g., having an average molecular weight below 5,000 g/m, has marginal emulsification capacity at best. Microspheres produced with such gelatin do not have adequate physical rigidity to result in a storage-stable product. Low Bloom gelatin within the range from about 25 to about 75 Bloom yields better emulsions with decreasing Bloom value, because the microdroplet particle size can be made progressively smaller.

The gelatin to be employed for microemulsification should also have a Bloom gel strength between about 25 and about 75 where a catch-medium process is used. Although stringiness and flaking would not likely occur in the process if high Bloom gelatin were used, gelatin having Bloom strength between about 25 and about 75 is preferred because it results in an emulsion characterized by smaller microdroplet size.

Where the Bloom gel strength of the gelatin to be employed is above about 75, a suitable hydrolysis operation is carried out to accordingly lower the gel strength. Preferably, acid hydrolysis is used, although controlled enzymatic hydrolysis may be suitably employed. Base hydrolysis is also well known in the gelatin art, but it is to be avoided because attendant deamination of end groups in the gelatin chemical structure results in release of ammonia, imparting an unpleasant odor even when only a minor concentration remains in the end product.

High Bloom gelatin having any gel strength can be employed as starting material, e.g., up to about 300 Bloom. However, low Bloom gelatin (i.e., having a Bloom value of about 200 or below) is preferred because high Bloom gelatin may be a prohibitively expensive raw material.

Where acid hydrolysis is to be carried out, the gelatin is dissolved in water with constant stirring and heated, e.g., to about 170° F. to about 185° F. Next, the gelatin is partially hydrolyzed with an inorganic acid. Sulfuric, phosphoric, and hydrochloric acids, for example, are suitable. The pH of the solution is adjusted to between about 3 to about 4, the temperature is maintained at between about 170° F. to about 185° F., and the operation is continued for several hours. Required reaction time varies with the starting Bloom value and the desired endpoint Bloom value. Those skilled in the gelatin art are readily able to determine the necessary processing times.

Alternatively, gelatin may be degraded to a material having a suitable Bloom gel strength by controlled enzymatic hydrolysis. Proteolytic enzymes, such as papain, bromelain, and ficin, are suitable. For example, 0.4 grams bromelain (1100 BTU) and 0.4 grams papain USP (46,000 units/mg) per 1,000 grams of 125 Bloom gelatin are dissolved in 1,000 gram of hot water at 150°-160° F. The solution is maintained at this temperature for 30 minutes, and the temperature is then raised to 170°-185° F. to destroy any remaining active enzyme. If desired, the enzyme can also be destroyed at the appropriate reaction end point by addition of hydrogen peroxide. Enzyme hydrolysis breaks down the gelatin molecular structure differently from acid hydrolysis, and the hydrolyzed product is generally less preferred for use than acid-hydrolyzed gelatin with the same Bloom value. Excessively vigorous enzymatic hydrolysis can result in gelatin of very low molecular weight which is devoid of emulsifying capacity and cannot be used.

Regardless of which hydrolysis process is employed, the conditions must be controlled and the reaction terminated at a desired point to prevent over-degradation.

If desired, a mixture of two or more gelatin types having different Bloom gel strengths can be used. For example, good results can be achieved using a 50/50 (w/w) mixture of acid-hydrolyzed gelatin (100-125 Bloom) and commercial enzymatically-hydrolyzed gelatin (5,000 average g/m, zero Bloom).

Where a double dispersion beadlet process is to be used instead of spray-drying or a catch-medium process (as explained below), high Bloom gelatin is employed, usually without hydrolysis. In this process, the gelatin-encased microdroplets are solidified by cooling rather than by atomization. High Bloom gelatin is more readily solidified in this manner than is low Bloom gelatin. Preferably, the Bloom value ranges from about 250 to about 300 Bloom.

Where a compressed-type product is to be made, the tableting characteristics of the microemulsified marine animal oil can be enhanced by adding a filler-binder to the marine animal oil and gelatin raw materials. Any non-toxic material which does not interfere with the microemulsification or adversely affect the chemical stability of the marine animal oil, may be employed. The preferred filler-binder, widely used in the pharmaceutical industry, is microcrystalline cellulose. Other suitable filler-binders include calcium phosphate, sodium silicate (e.g., MicroCel E made by Johns-Manville), calcium sulfate (terra alba), and hydroxypropylmethyl cellulose.

Further optional ingredients include conventional antioxidants, flavorings and colorings. Suitable antioxidants include d-alpha-tocopherol, TBHQ (monotertiary-butyl hydroquinone), BHA (butylated hydroxyanisole), BHT (butylated hydroxytoluene), ascorbyl palmitate, and propyl gallate. Although antioxidants are optional, as a practical matter they are always added to marine animal oils. Even under optimum dark, cool, anaerobic storage conditions, marine animal oils rapidly deteriorate in their absence. Normally, an antioxidant is added in a minor amount, up to about 0.5% by weight of the microspheres or macrospheres. However, higher percentages of certain antioxidants may be desirable for particular product applications.

The proportions of marine animal oil and gelatin are tailored to particular needs. Broadly, the marine animal oil may be present in the microemulsified product in any amount up to about 70% by weight. Microemulsification of a composition comprising more than about 70% by weight marine animal oil is not advisable, because the oil will tend to migrate out of the microspheres or macrospheres due to syneresis and bleeding. There is no lower limit on the amount of marine animal oil which can be used. However, as a practical matter some reasonable lower limit will be established because the marine animal oil is the active ingredient of the composition. Preferably, the marine animal oil constitutes at least about 5% by weight of the composition of the microemulsified product. More preferably, the marine animal oil constitutes about 25% to about 70% by weight of the composition of the microemulsified product.

Where a spray-drying process is used, the marine animal oil still more preferably constitutes about 50% to about 70% by weight of the composition, and most preferably about 50% to about 55% by weight. Where a catch-medium process or a double-dispersion beadlet process is used, the marine animal oil still more preferably constitutes about 25% to about 50% by weight of the composition, and most preferably about 35% by weight.

The gelatin microemulsifier must be present in an amount sufficient to yield a stable microemulsion to contain the marine animal oil. The only upper limitation on the amount of gelatin to be used is the proportion of marine animal oil desired in the product. Preferably, where spray-drying is employed, the gelatin constitutes about 50% to about 30% by weight of the composition. More preferably, the gelatin constitutes about 50% to about 45% by weight of the composition. Where a catch-medium process or double dispersion beadlet process is used, the gelatin preferably constitutes about 75% to about 50% by weight, and most preferably about 65% by weight.

Where it is desired to incorporate a filler-binder into the composition as a tableting aid, the proportion to be employed is dictated by the chosen minimum proportions of marine animal oil and gelatin. For example, if it is desired to employ at least 50% marine animal oil and at least 40% gelatin, then the filler-binder may constitute up to 10% by weight of the composition.

One preferred composition for a microemulsified marine animal oil to be incorporated in a compressed tablet-type solid form product (e.g., tablets, caplets, hardshell capsules or the like) consists essentially of about 50% by weight of marine animal oil, about 45% by weight of gelatin microemulsifier, and about 5% by weight of microcrystalline cellulose. A preferred composition for a free-flowing, uncompressed microemulsified product consists essentially of about 50% by weight of marine animal oil, about 45% to about 49% by weight of gelatin, and about 5% to about 1% by weight of microcrystalline cellulose. Other compositions may be readily determined by those skilled in the art using the guidelines set forth above.

As one typical example, a tableted product can be made including the following ingredients: microemulsified marine animal oil (500 mg), Syloid 74 silicon dioxide (Davison Chemical Co.) (30 mg), Cab-O-Sil M-5 silicon dioxide (made by Cabot) (6 mg), Micro-Cel E (Johns Manville) sodium silicate (12 mg) and Ditab dibasic calcium phosphate (Stauffer Chemical Co.) (75 mg).

The microemulsified marine animal oils of the invention can also be incorporated into multivitamin tablet-type formulations. For example, a tablet may be made incorporating about 100 milligrams to about 300 milligrams of dry microemulsified marine animal oil, the balance being a conventional multinutrient formulation.

Once the composition proportions to be employed have been chosen, the ingredients are combined to produce an emulsion suitable to be converted to a microemulsified product. Advantageously, the gelatin having an appropriate Bloom strength for the chosen drying process is first dissolved in hot water with stirring. Preferably, the water is maintained at a temperature between about 170° F. and about 185° F. (to avoid growth of bacteria), and the amount of water employed should be equal to about 40% to about 50% based on the weight of the gelatin to be employed. The marine animal oil is then added, and the solution is homogenized to form an oil-in-water emulsion. The marine animal oil forms a discontinuous phase which is surrounded by an aqueous gelatin continuous phase. The gelatin is a protective colloid: it prevents the marine animal oil microdroplets from coalescing into larger droplets.

The particle size of the marine animal oil discontinuous phase microdroplets which are contained in the aqueous gelatin continuous phase is an important factor in determining the quality of the microemulsified product. If the particle size of the marine animal oil microdroplets is excessively large, the microemulsified product will tend to be physically unstable because of syneresis and bleeding of the microdroplets.

The microemulsification process is monitored, e.g. by diluting a one-gram sample of the microemulsion in 100 grams of warm water and microscopically evaluating dispersed particle size. Preferably, the maximum observed dispersed particle size is about 5 microns in diameter. More preferably, the maximum observed dispersed particle size is about 3 microns in diameter. Particles smaller than about one micron in size vastly outnumber the largest particles. However, since the particles are desirably as small as possible, only the maximum observed dispersed particle size is monitored. In the case of tablet-type solid product forms, the maximum observed dispersed particle size is particularly important. Relatively small dispersed particles will tend to better withstand the compression forces necessary to produce a tablet-type product. These forces may be on the order of four tons per square inch.

Where the gelatin has been hydrolyzed using a mineral acid, it should be neutralized, e.g., by addition of a base such as a 20% aqueous potassium- or sodium-hydroxide solution, to a pH of about 6.0 to 6.5. This can be done at any point after the hydrolysis reaction is complete.

In one embodiment, a spoonable drinkable emulsion is made using low molecular weight (zero-Bloom) gelatin, and is employed as a food product without converting it into microspheres or macrospheres. For example, flavorings, sweeteners and natural gums can be added to the emulsion to produce a marine animal oil drink product. The superior taste and texture (i.e., mouth feel) of the emulsions of the invention make them highly suitable for such use. In a particular embodiment, a microemulsified, Omega-three acid-containing oil composition is prepared consisting essentially of (1) a solids phase comprising (A) up to about 70% by weight of Omega-three acid-containing oil, and (B) gelatin, in which the oil is microemulsified by the gelatin; and (2) an aqueous phase.

In further embodiments, after suitable homogenization to yield an acceptable particle size, the emulsion is next subdivided into dry microdroplets, either as microspheres or macrospheres. Preferably, this subdivision is carried out by a spray-drying operation.

Before spray-drying, the solids content of the oil-in-water emulsion is lowered, if necessary, by dilution with water. Preferably, the total solids content of the emulsion is adjusted to about 40% to about 50% by weight. The viscosity of the emulsion is also advantageously adjusted to be between about 200 centipoises and about 800 centipoises. Viscosities can be measured conventionally using a Brookfield viscometer. If desired, filler-binders are added to the emulsion, with stirring.

In order to spray-dry the microdroplets, the hot, dilute emulsion is atomized in the spray chamber of a spray-drying apparatus and rapidly dried in a drying chamber with a heated high velocity air stream. Preferably, the inlet temperature of the high velocity air stream into the spray chamber in the atomizer is between about 400° F. to about 450° F.; and the temperature at the outlet from the spray chamber is preferably between about 195° F. to about 205° F. Centrifugal and pressure-type atomizers can be used. A suitable speed for commercial centrifugal atomizers is about 12,000 rpm to about 20,000 rpm, more preferably about 15,000 rpm.

The product from a spray-drying process consists of microspheres varying in size, having a diameter ranging from about 50 microns to about 400 microns and preferably ranging from about 200 microns to about 300 microns. Each microsphere on average consists of several hundred gelatin-encased marine animal oil microdroplets. This microsphere structure is highly stable against syneresis and bleeding, since each marine animal oil microdroplet is individually encased in gelatin.

In a preferred embodiment, the moist spray-dried product is agglomerated by after-treatment in a separate fluid bed dryer or in an integrated fluid bed drying system, to further improve tablet compressibility.

If desired, a flow agent such as silicon dioxide can be metered into the drying chamber of the spray-dryer. This powder coats the outside of the microspheres, resulting in optimum microsphere fluidization and keeping the drying chamber clean.

A second embodiment involves a catch-medium process. Catch-medium drying processes are known in the art. In this embodiment, gelatin having gel strength between about 25 to about 75 Bloom is employed. According to this embodiment, the marine animal oil-in-water emulsion is subdivided into microdroplets with a suitable atomizer. This is carried out as described earlier, except that the atomizer is one adapted for use in a conventional catch-medium process. The microdroplets form airborne macrospheres. These macrospheres are structurally similar to the microspheres discussed above in connection with spray-drying, except that they are about ten times greater in volume. Hence, each macrosphere contains, on average, several thousand marine animal oil microdroplets, each microdroplet individually encased in gelatin. These macrospheres vary in size, their diameter typically ranging from about 200 microns to about 1000 microns. They are also more dense than the microspheres. To prevent their coalescence, the macrospheres are directed into a catch-medium capable of keeping the macrospheres apart. The catch-medium may be a fluidized solid (e.g., dried starch with silicon dioxide, or a hydrophobic starch ester) or a continuously agitated liquid material, such as mineral oil, vegetable oil or a lower alcohol. Hydrophobic starch esters and lower alcohols are preferred. More preferably, such an ester or lower alcohol, blended with about 1% to about 2% by weight of silicon dioxide, based on the weight of ester or alcohol, is employed. Where a solid catch-medium is employed, the macrospheres are separated from it by sifting. Where the catch-medium is a liquid, the macrospheres are separated by filtration, washed with a suitable solvent and dried.

In a third embodiment, the emulsion is converted, by a double dispersion beadlet process, into free-flowing dried macrospheres similar to those produced using a catch-medium. Double dispersion beadlet drying processes are known in the art. According to this embodiment, gelatin having a Bloom gel strength between about 250 and about 300 is employed. In the process, the oil-in-water emulsion is finely divided with suitable homogenization into mineral oil (or another suitable medium, as known to those skilled in the art). This yields a suspension of marine animal oil-containing gelatin macrospheres in the mineral oil. The suspension is cooled to solidify the macrospheres, and the macrospheres are separated from the mineral oil by filtration, washed with suitable solvents, and dried.

The marine animal oil free-flowing microemulsified microsphere and macrosphere compositions of this invention have wide-ranging utility. For example, a microsphere or macrosphere product may be converted to tablet-type solid form. Tablets, caplets, hardshell capsules and the like can be made. Those skilled in the art of converting powdered compositions into tablet-type solid form will readily be able to make such products from the compositions of the invention. Alternatively, the microsphere and macrophere compositions can be incorporated in particulate form into food products for human or animal consumption.

The following examples further illustrate the present invention in detail, but are not to be construed in any way to limit the scope thereof.

EXAMPLE 1

A measured amount (525 kg.) of low Bloom gelatin (125 Bloom) was dissolved with constant stirring in 550 kg. of water heated to between about 170° F. to about 185° F. Hydrochloric acid (19 kg.) was then added with stirring, and the acidulated hot solution (pH about 3.5 to about 4) was continuously stirred and heated for five hours. Marine animal oil (570 kg.) was slowly emulsified into the solution with an Arde Barinco Reversible Homogenizer over a period of 1 hour. After the particle size was reduced to a maximum of about 5 microns, the emulsion was diluted with sufficient water to bring the total solids to about 45% by weight. Microcrystalline cellulose (11 kg.) was then added to the emulsion with the Arde Homogenizer set in the downward "vortex" flow position. Next, the emulsion was neutralized with a 20% aqueous potassium hydroxide solution to a pH between about 6.0 and 6.5. The emulsion was then spray-dried in a commercial spray-dryer (14 ft. diameter flat-bottom Bowen unit). A centrifugal atomizer (DH-8" wheel) was employed, at a speed of 15,000 rpm. The spray chamber inlet temperature was maintained at 400°-450° F. and the outlet temperature at 195°-205° F. The microspheres ejected from the spray-dryer were then blended with 1-2% silicon dioxide by weight, based on the weight of the dry microemulsified powder. Antioxidant (d-alpha-tocopherol) was added in a minor amount (about 0.2% based on the weight of the marine animal oil).

EXAMPLE 2

Low Bloom gelatin (500 grams, 100-125 Bloom) and hydrolyzed gelatin (500 grams, average molecular weight 5000, zero Bloom) were dissolved with stirring into 1,000 grams of water heated to between 170° F. and 185° F. Marine animal oil (1300 grams) Was slowly homogenized into the hot gelatin solution. After suitable homogenization to reduce the particle size, the emulsion was diluted with 1,270 grams of warm water to a total solids content of about 50%. Next, Micro-Cel E (calcium silicate) (24 grams) was added with stirring. The emulsion was then spray-dried using a 3 ft. diameter laboratory Boeen spray-dryer. The spray-dried microemulsified product was then blended with 2% silicon dioxide by weight. Antioxidant was added as in Example 1.

EXAMPLE 3

Low Bloom gelatin (500 grams, 125 Bloom) was dissolved with stirring in 500 grams water heated to 140°-150° F. With continuous stirring, 0.2 grams of bromelain (1100 BTU/gram) and 0.2 grams of papain (46,000 USP units/mig.) were added. The mixture was maintained at between 140° F. to 150° F. for thirty minutes, after which the temperature was raised to 170° F. to 185° F. Marine animal oil (610 grams) was then slowly homogenized into the hot, enzymatic hydrolyzate. After the particle size was suitably reduced by the homogenization, the emulsion was diluted with 620 grams of water. With continued stirring, microcrystalline cellulose (15 grams) was added. The emulsion was then spray-dried using a 3 ft. diameter laboratory Bowen spray-dryer, at an inlet temperature of 400° F. and an outlet temperature of 225° F., and a centrifugal atomizer speed of 50,000 rpm. Antioxidant was added as in Example 1.

EXAMPLE 4

Type A low Bloom gelatin (500 grams, less than 50 Bloom) was dissolved with stirring in 500 grams of water heated to between 150° F. and 165° F. Marine animal oil (610 grams) was slowly homogenized into the gelatin solution. After suitable homogenization to reduce the particle size, the emulsion was diluted with 800 grams of warm water. Microcrystalline cellulose (12 grams) was then added with stirring. The emulsion was spray-dried as in Example 1 in the presence of Micro-Cel E which was directly metered into the drying chamber at a rate constituting about 1-2% by weight of the microemulsified product. Antioxidant was added as in Example 1.

ACCELERATED AGING TEST

The microemulsified product of Example 1 (Test Sample #1) was subjected to accelerated aging tests in order to simulate storage for an extended period of time. These tests were carried out by storing samples of the product at 45° C. in open, shallow storage vessels. Storage of a test specimen at 45° C. is considered to simulate three months of real time aging per week of storage. An emulsion of marine animal oil in modified food starch was spray-dried as in Example 1 to yield a particulate product which was employed as a Comparative Example. Modified food starch is widely used to prepare spray-dried, coated, particulate products.

| Sample | Percentage Retention of DHA and EPA After Storage | | | | |
|---|---|---|---|---|---|
| | Initial | 1 week | 2 weeks | 3 weeks | 4 weeks |
| Example #1 | 100 | 100 | 100 | 96 | 94 |
| Comparative Example | 100 | 30 | 37 | 26 | 20 |

These accelerated aging tests show that after four weeks of accelerated aging, equivalent to one year in real time, Example #1 according to the invention retained 94% of its DHA and EPA. On the other hand, in the Comparative Example, only 20% of the DHA and EPA remained; the other 80% had degraded.

Although the presently-preferred embodiments of the invention have been set forth, it will be understood by those skilled in the art that modifications can be made without departing from the principles of the invention. Accordingly, the present invention should be understood as encompassing all such modifications as are within the spirit and scope of the following claims.

What is claimed is:

1. A storage-stable, bio-available, free-flowing, microemulsified, Omega-three acid-containing oil composition in a form selected from the group consisting of microspheres and macrospheres, said composition consisting essentially of (1) up to about 70% by weight of Omega-three acid-containing oil, and (2) gelatin, in which the oil is microemulsified by the gelatin.

2. The composition of claim 1 consisting essentially of about 25% to about 70% by weight of Omega-three acid-containing oil, and about 75% to about 30% by weight of gelatin.

3. The composition of claim 1 in the form of microspheres having a diameter ranging from about 50 microns to about 400 microns, and in which the gelatin has a Bloom value between about 25 and about 75, said microspheres being produced by spray-drying.

4. The composition of claim 3, in which the microspheres consist essentially of about 50% to about 70% by weight of Omega-three acid-containing oil, microemulsified by about 50% to about 30% by weight of gelatin.

5. The composition of claim 1 in the form of macrospheres having a diameter ranging from about 200 microns to about 1000 microns, and in which the gelatin has a Bloom value between about 25 and about 75, said macrospheres being produced by a catch-medium process.

6. The composition of claim 5 in which the macrospheres consist essentially of about 25% to about 50% by weight of Omega-three acid-containing oil and about 75% to about 50% by weight of gelatin.

7. The composition of claim 1 in the form of macrospheres having a diameter ranging from about 200 microns to about 1000 microns, and in which the gelatin has a Bloom value between about 250 and about 300, said macrospheres being produced by a double-dispersion beadlet process.

8. The composition of claim 7 in which the macrospheres consist essentially of about 25% to about 50% by weight of Omega-three acid-containing oil and about 75% to about 50% by weight of gelatin.

9. The composition of claim 1 comprising up to about 10% by weight of a filler-binder.

10. The composition of claim 1 comprising up to about 0.5% by weight of an anti-oxidant.

11. The composition of claim 3, 5 or 7 compressed into a tablet form.

12. A process of making a storage-stable, bio-available, free-flowing, microemulsified, Omega-three acid-containing oil composition in microsphere form, comprising the steps of:
   (A) Combining with homogenization, (1) up to about 70% by weight of Omega-three acid-containing oil, and (2) gelatin having a Bloom value between about 25 and about 75, to yield an oil-in-water emulsion thereof;
   (B) Homogenizing the emulsion until the maximum observed dispersed particle diameter is about 5 microns or less;
   (C) Adding sufficient water to the emulsion so that the combined weight of Omega-three acid-containing oil and gelatin is about 40% to about 50% of the total weight of the emulsion; and
   (D) Spray-drying the emulsion to yield a dry, microemulsified Omega-three acid-containing oil composition, in which the oil is microemulsified by the gelatin in microspheres having a diameter ranging from about 50 microns to about 400 microns.

13. The process of claim 12 which comprises combining with homogenization (1) about 25% to about 70% by weight of Omega-three acid-containing oil, and (2) about 75% to about 30% by weight of gelatin.

14. The process of claim 12 which comprises combining with homogenization (1) about 50% to about 70% by weight of Omega-three acid-containing oil, and (2) about 50% to about 30% by weight of gelatin.

15. The process of claim 11 comprising combining up to about 10% by weight of a filler-binder with the emulsion prior to spray-drying.

16. The process of claim 12 comprising combining an anti-oxidant with the emulsion prior to spray-drying, in an amount up to about 0.5%.

17. The process of claim 12 comprising compressing the microspheres into tablet form.

18. A microemulsified, Omega-three acid-containing oil composition consisting essentially of (1) a solids phase comprising (A) up to about 70% by weight of Omega-three acid-containing oil, and (B) gelatin, in which the oil is microemulsified by the gelatin; and (2) an aqueous phase.

* * * * *

UNITED STATES PATENT AND TRADEMARK OFFICE
CERTIFICATE OF CORRECTION

PATENT NO. : 4,867,986

DATED : September 19, 1989

INVENTOR(S) : Desai et al.

It is certified that error appears in the above-identified patent and that said Letters Patent is hereby corrected as shown below:

Col. 10, line 14, change "mig." to --mg.--.

Col. 12, line 8, Claim 11, after "into" delete "a".

Signed and Sealed this

Thirteenth Day of November, 1990

Attest:

HARRY F. MANBECK, JR.

*Attesting Officer*     *Commissioner of Patents and Trademarks*